(12) United States Patent
Foerster

(10) Patent No.: US 10,765,418 B2
(45) Date of Patent: Sep. 8, 2020

(54) KNOTLESS DYNAMIC SUTURE TENSIONING DEVICE AND METHODS

(71) Applicant: Zimmer, Inc., Warsaw, IN (US)

(72) Inventor: Seth A Foerster, San Clemente, CA (US)

(73) Assignee: Zimmer, Inc., Warsaw, IN (US)

( * ) Notice: Subject to any disclaimer, the term of this patent is extended or adjusted under 35 U.S.C. 154(b) by 216 days.

(21) Appl. No.: 15/821,486

(22) Filed: Nov. 22, 2017

(65) Prior Publication Data

US 2018/0092637 A1 Apr. 5, 2018

Related U.S. Application Data

(60) Continuation of application No. 14/137,533, filed on Dec. 20, 2013, now Pat. No. 9,844,365, which is a division of application No. 12/406,902, filed on Mar. 18, 2009, now Pat. No. 8,613,755.

(60) Provisional application No. 61/037,582, filed on Mar. 18, 2008.

(51) Int. Cl.
  *A61B 17/04* (2006.01)
(52) U.S. Cl.
  CPC .............................. *A61B 17/0401* (2013.01)
(58) Field of Classification Search
  CPC ............ A61B 17/0487; A61B 17/0401; A61B 2017/0496; A61B 2017/0446
  See application file for complete search history.

(56) References Cited

U.S. PATENT DOCUMENTS

| | | | |
|---|---|---|---|
| 55,854 A | 6/1866 | Gunning et al. |
| 93,592 A | 8/1869 | Heman |
| 286,264 A | 10/1883 | Clough |
| 303,360 A | 8/1884 | Friedrich et al. |
| 357,597 A | 2/1887 | Hazelton |
| 405,958 A | 6/1889 | Hall et al. |
| 421,354 A | 2/1890 | Fish |
| 423,000 A | 3/1890 | Turnbull |
| 434,926 A | 8/1890 | Hall |
| 627,489 A | 6/1899 | Ekstrand et al. |
| 651,812 A | 6/1900 | Krause et al. |
| 663,877 A | 12/1900 | Friedenberg |
| 685,252 A | 10/1901 | Bugbee et al. |

(Continued)

OTHER PUBLICATIONS

U.S. Appl. No. 12/406,904 U.S. Pat. No. 8,303,591, filed Mar. 18, 2019, Load Shaping For Dynamic Tensioning Mechanisms and Methods.

(Continued)

*Primary Examiner* — Dianne Dornbusch
(74) *Attorney, Agent, or Firm* — Schwegman Lundberg & Woessner, P.A.

(57) ABSTRACT

Two spaced bodily tissues are approximated with a surgical tensioning device comprising a resilient member and a pressure locking device. The method comprises a step of routing one end of a length of suture through both spaced bodily tissues and inserting the suture end into and through the pressure locking device. The suture is then tensioned by pulling on the suture end passing through the pressure locking device. Responsive to tension changes in the suture, the pressure locking device is actuated by moving at least one surface in the pressure locking device to clamp the suture in position.

17 Claims, 3 Drawing Sheets

(56) References Cited

U.S. PATENT DOCUMENTS

| | | | |
|---|---|---|---|
| 699,790 A | 5/1902 | Collins | |
| 714,579 A | 11/1902 | Hecht et al. | |
| 875,102 A | 12/1907 | Peterson et al. | |
| 886,732 A | 5/1908 | Sawtell | |
| 919,947 A | 4/1909 | Plowman | |
| 950,434 A | 2/1910 | Carlson et al. | |
| 988,617 A | 4/1911 | Bair et al. | |
| 1,045,174 A | 11/1912 | Perrine | |
| 1,056,211 A | 3/1913 | Peterson | |
| 1,079,080 A | 11/1913 | Ward et al. | |
| 1,187,836 A | 6/1916 | Hoekstra et al. | |
| 1,219,283 A | 3/1917 | Frantz et al. | |
| 1,279,206 A | 9/1918 | Wolff | |
| 1,400,178 A | 12/1921 | Perrine et al. | |
| 1,538,611 A | 5/1925 | Beichl | |
| 1,779,449 A | 10/1930 | Adam | |
| 1,886,917 A | 11/1932 | St. Pierre | |
| 1,999,168 A | 4/1935 | Erb | |
| 2,081,385 A | 5/1937 | Bligh | |
| 2,307,120 A | 1/1943 | Henry | |
| 2,386,251 A | 10/1945 | Mefford | |
| 2,552,957 A | 5/1951 | Gore | |
| 2,628,399 A * | 2/1953 | Gore | A41F 1/00 |
| | | | 24/308 |
| 2,965,942 A | 12/1960 | Carter | |
| 2,977,655 A | 4/1961 | Peters | |
| 2,981,994 A | 5/1961 | White | |
| 3,112,543 A | 12/1963 | Derrickson | |
| 3,226,791 A | 1/1966 | Garter | |
| 3,822,445 A | 7/1974 | Feng | |
| 3,967,347 A | 7/1976 | Bickis, Sr. | |
| 4,279,248 A | 7/1981 | Gabbay | |
| 4,444,181 A | 4/1984 | Wevers et al. | |
| 4,535,772 A | 8/1985 | Sheehan | |
| 4,667,675 A | 5/1987 | Davis | |
| 4,670,945 A | 6/1987 | Banks et al. | |
| 4,730,615 A | 3/1988 | Sutherland et al. | |
| 4,813,416 A | 3/1989 | Pollak et al. | |
| 4,840,093 A | 6/1989 | Goldman, Jr. | |
| 4,901,721 A | 2/1990 | Hakki | |
| 4,938,760 A | 7/1990 | Burton et al. | |
| 4,959,064 A | 9/1990 | Engelhardt | |
| 4,969,892 A | 11/1990 | Burton et al. | |
| 5,063,641 A | 11/1991 | Chuan et al. | |
| 5,161,351 A * | 11/1992 | Woodruff | A44B 11/14 |
| | | | 24/170 |
| 5,173,996 A | 12/1992 | Chou | |
| 5,258,015 A * | 11/1993 | Li | A61B 17/0401 |
| | | | 128/912 |
| 5,282,832 A * | 2/1994 | Toso | A61B 17/0487 |
| | | | 24/DIG. 50 |
| 5,330,489 A | 7/1994 | Green et al. | |
| 5,339,870 A | 8/1994 | Green et al. | |
| 5,366,461 A | 11/1994 | Blasnik | |
| 5,571,105 A | 11/1996 | Gundolf | |
| 5,593,009 A | 1/1997 | King | |
| 5,722,976 A | 3/1998 | Brown | |
| 5,797,915 A | 8/1998 | Pierson, III et al. | |
| 5,807,214 A | 9/1998 | Riazi | |
| 5,810,854 A | 9/1998 | Beach | |
| 5,849,012 A | 12/1998 | Abboudi | |
| 5,972,006 A | 10/1999 | Sciaino, Jr. | |
| 6,051,007 A | 4/2000 | Hogendijk et al. | |
| 6,066,160 A | 5/2000 | Colvin et al. | |
| 6,080,185 A | 6/2000 | Johnson et al. | |
| 6,471,715 B1 | 10/2002 | Weiss et al. | |
| 6,540,729 B1 | 4/2003 | Wada | |
| 6,540,769 B1 | 4/2003 | Miller, III | |
| 6,547,725 B1 | 4/2003 | Paolitto et al. | |
| 6,589,246 B1 | 7/2003 | Hack et al. | |
| 6,631,539 B1 | 10/2003 | Chang | |
| 6,648,903 B1 * | 11/2003 | Pierson, III | A61B 17/0401 |
| | | | 606/232 |
| 6,969,398 B2 | 11/2005 | Stevens et al. | |
| 6,997,189 B2 | 2/2006 | Biggs et al. | |
| 7,108,710 B2 | 9/2006 | Anderson | |
| 7,341,558 B2 | 3/2008 | De La Torre et al. | |
| 7,416,556 B2 | 8/2008 | Jackson | |
| 7,722,632 B2 * | 5/2010 | Rothstein | A61B 17/0483 |
| | | | 606/148 |
| 980,701 A1 | 1/2011 | Swafford et al. | |
| 7,867,251 B2 | 1/2011 | Colleran et al. | |
| 7,867,253 B2 | 1/2011 | Mcmichael et al. | |
| 7,938,847 B2 * | 5/2011 | Fanton | A61B 17/0401 |
| | | | 600/300 |
| 8,303,591 B1 | 11/2012 | Foerster | |
| 8,613,755 B1 | 12/2013 | Foerster | |
| 8,790,344 B1 | 7/2014 | Foerster | |
| 9,844,365 B1 | 12/2017 | Foerster | |
| 2002/0147449 A1 | 10/2002 | Yun | |
| 2003/0093117 A1 | 5/2003 | Saadat | |
| 2004/0098050 A1 * | 5/2004 | Foerster | A61B 17/0401 |
| | | | 606/232 |
| 2005/0075653 A1 | 4/2005 | Saadat et al. | |
| 2005/0090827 A1 * | 4/2005 | Gedebou | A61B 17/0401 |
| | | | 606/232 |
| 2005/0149121 A1 | 7/2005 | Crombie | |
| 2005/0240203 A1 | 10/2005 | Fuseri et al. | |
| 2005/0245945 A1 * | 11/2005 | Ewers | A61B 1/00135 |
| | | | 606/153 |
| 2005/0251209 A1 * | 11/2005 | Saadat | A61B 17/0401 |
| | | | 606/232 |
| 2007/0073289 A1 | 3/2007 | Kwak et al. | |
| 2007/0112385 A1 | 5/2007 | Conlon | |
| 2007/0213725 A1 | 9/2007 | Hack | |
| 2007/0276437 A1 * | 11/2007 | Call | A61B 17/0487 |
| | | | 606/232 |
| 2007/0293863 A1 | 12/2007 | Reimels et al. | |
| 2007/0293864 A1 | 12/2007 | Reimeis et al. | |
| 2008/0004624 A1 | 1/2008 | Olroyd | |
| 2008/0015589 A1 | 1/2008 | Hack | |
| 2009/0062853 A1 | 3/2009 | Mcmichael et al. | |

OTHER PUBLICATIONS

U.S. Appl. No. 13/650,996 U.S. Pat. No. 8,709,344, filed Oct. 12, 2012, Load Shaping For Dynamic Tensioning Mechanisms and Methods.

U.S. Appl. No. 12/406,902 U.S. Pat. No. 8,613,755, filed Mar. 18, 2019, Knotless Dynamic Suture Tensioning Device and Methods.

U.S. Appl. No. 14/137,533, filed Dec. 20, 2013, Knotless Dynamic Suture Tensioning Device and Methods.

"U.S. Appl. No. 12/406,902, Decision on Appeal dated May 9, 2013", 2 pgs.

"U.S. Appl. No. 12/406,902, Examiner Interview Summary dated Jul. 19, 2012", 7 pgs.

"U.S. Appl. No. 12/406,902, Non Final Office Action dated Jan. 24, 2012", 9 pgs.

"U.S. Appl. No. 12/406,902, Non Final Office Action dated Jul. 6, 2012", 12 pgs.

"U.S. Appl. No. 12/406,902, Notice of Allowance dated Aug. 19, 2013", 10 pgs.

"U.S. Appl. No. 12/406,902, Notice of Non-Compliant Amendment dated Nov. 22, 2011", 2 pgs.

"U.S. Appl. No. 12/406,902, Pre-Brief Conference request filed Apr. 9, 2013", 7 pgs.

"U.S. Appl. No. 12/406,902, Response filed May 24, 2012 to Non Final Office Action dated Jan. 24, 2012", 8 pgs.

"U.S. Appl. No. 12/406,902, Response filed Oct. 8, 2012 to Non Final Office Action dated Jul. 6, 2012", 9 pgs.

"U.S. Appl. No. 12/406,902, Response filed Oct. 13, 2011 to Restriction Requirement dated Sep. 14, 2011", 1 pg.

"U.S. Appl. No. 12/406,902, Response filed Dec. 22, 2011 to Notice of Non-Compliant Amendment dated Nov. 22, 2011", 5 pgs.

"U.S. Appl. No. 12/406,902, Restriction Requirement dated Sep. 14, 2011", 8 pgs.

"U.S. Appl. No. 12/406,904, Non Final Office Action dated Dec. 7, 2011", 8 pgs.

(56) References Cited

OTHER PUBLICATIONS

"U.S. Appl. No. 12/406,904, Notice of Allowance dated Jul. 18, 2012", 9 pgs.

"U.S. Appl. No. 12/406,904, Response filed May 7, 2012 to Non Final Office Action dated Dec. 7, 2011", 8 pgs.

"U.S. Appl. No. 12/406,904, Response filed Oct. 13, 2011 to Restriction Requirement dated Sep. 14, 2011", 1 pg.

"U.S. Appl. No. 12/406,904, Restriction Requirement dated Sep. 14, 2011", 6 pgs.

"U.S. Appl. No. 13/650,996, Notice of Allowance dated Mar. 20, 2014", 8 pgs.

"U.S. Appl. No. 13/650,996, Preliminary Amendment filed Jan. 7, 2013", 5 pgs.

"U.S. Appl. No. 13/650,996, Preliminary Amendment filed Mar. 28, 2013", 3 pgs.

"U.S. Appl. No. 13/650,996, Response filed Jul. 8, 2013 to Restriction Requirement dated Apr. 8, 2013", 2 pgs.

"U.S. Appl. No. 13/650,996, Restriction Requirement dated Apr. 8, 2013", 5 pgs.

"U.S. Appl. No. 14/137,533, Advisory Action dated May 31, 2017", 4 pgs.

"U.S. Appl. No. 14/137,533, Final Office Action dated Mar. 2, 2017", 7 pgs.

"U.S. Appl. No. 14/137,533, Non Final Office Action dated Nov. 22, 2016", 10 pgs.

"U.S. Appl. No. 14/137,533, Notice of Allowance dated Aug. 23, 2017", 8 pgs.

"U.S. Appl. No. 14/137,533, Preliminary Amendment filed Mar. 6, 2014", 7 pgs.

"U.S. Appl. No. 14/137,533, Response filed Feb. 3, 2017 to Non Final Office Action dated Nov. 22, 2016", 12 pgs.

"U.S. Appl. No. 14/137,533, Response filed May 2, 2017 to Final Office Action dated Mar. 2, 2017", 11 pgs.

"U.S. Appl. No. 14/137,533, Response filed Oct. 7, 2016 to Restriction Requirement dated Apr. 20, 2016".

"U.S. Appl. No. 14/137,533, Restriction Requirement dated Apr. 20, 2016", 8 pgs.

\* cited by examiner

KNOTLESS DYNAMIC SUTURE TENSIONING DEVICE AND METHODS

This application is a continuation of U.S. patent application Ser. No. 14/137,533, filed on Dec. 20, 2013, now issued as U.S. Pat. No. 9,844,365, which is a continuation of U.S. patent application Ser. No. 12/406,902, filed on Mar. 18, 2009, now issued as U.S. Pat. No. 8,613,755, which claims the benefit under 35 U.S.C. 119(e) of the filing date of Provisional U.S. Application Ser. No. 61/037,582, entitled Dynamic Ring Compression Device, filed on Mar. 18, 2008, and expressly incorporated herein by reference, in its entirety. This application is also related to U.S. patent application Ser. No. 12/347,821, now issued as U.S. Pat. No. 8,414,599, entitled Dynamic Suture Tensioning Device and filed on Dec. 31, 2008, entitled Load Shaping for Dynamic Tensioning Mechanisms and Methods, and A-2397, entitled Dynamic Tissue Holding Device with Low Profile Spring, both filed on even date herewith, all of which are commonly assigned and expressly incorporated herein, by reference, in their entirety.

BACKGROUND OF THE INVENTION

The present invention is related to the general surgical repair of separated body tissues, and more particularly to internally fixating and stabilizing such body tissues, specifically bones.

In the present state of the art, there are a number of systems available to repair biological tissues separated in surgery or by injury. These products serve to approximate and stabilize the tissues so that healing may commence and provide compression in the interface to promote healing. Compression and stability are critical for proper anatomical healing of tissue. With the correct amount of compression applied to the interface of the tissue portions to be joined, signals are sent to the tissue, thus allowing the tissue to remodel in proper anatomical position. The amount of compression applied to the tissue interface needs to be appropriate to the type of tissue that is being healed.

A common problem in using suture is the variable nature of the residual tension realized after the knot is tied. Hand tied knots usually supply only a fraction of the residual tension for which the suture is capable. There are various procedures where the residual tension in a hand tied knot is insufficient to approximate and generate the compression needed for healing between tissues. Moreover, knot stacks can interfere with the natural movement of surrounding tissues.

There are times when high tension may cause suture to cut into tissue at points of stress concentration. This suture cutting may not happen immediately. It can take place as the tissue degrades or relaxes, or sometimes there are external forces that cause the suture to cut into the tissue. This cutting action releases tension in the suture and adversely affects the quality and durability of the repair.

Additionally, the use of wires can cause damage to adjunctive tissues because of penetration by the sharp ends of the wires.

What is needed, therefore, are devices and techniques for holding two tissue portions in a state of compression and tension beyond that which is commonly achieved using hand-tied sutures.

SUMMARY OF THE INVENTION

The present invention solves the problems outlined above by providing a means to approximate two tissue portions together so that there is compression in the tissue interface. The invention provides a means to hold two tissues in a state of compression beyond that which is commonly achieved with the hand tying of sutures. The invention may also be used to lengthen retracted tendons or ligaments. This is done by anchoring one end of the suture on bone and the other end on tendon or a ligament. The dynamic tensioning element in the invention serves to stretch and optionally attach the tendon or ligament to the bone.

Attached to one end of the suture is a resilient mechanism designed to keep tension in the suture, as tissues will shrink during healing. This resilient mechanism lies on top of the tissues to be approximated. The free end of the suture is brought to the resilient mechanism and routed into an integral receptacle such that pulling on the suture end will bring the tissues together. As the tissues come together and tension is brought to the suture, the resilient mechanism will activate and start to store the energy needed to activate the resilient mechanism, in order to keep tension on the suture when the tissues shrink during healing.

When the desired suture tension has brought the tissues to their desired position for healing, a surface or surfaces within the suture receiving receptacle acts to put pressure on the suture. The pressure applied is sufficient to bind the suture end with the resilient mechanism. This surface, or these surfaces, within the suture receiving receptacle provide(s) latent pressure on the suture during the suture tensioning process. The latent pressure is then converted to a binding pressure, once the suture has approximated the tissues. This pressure conversion happens as a result of the change in tension on the suture as it is released from the practitioner's grasp.

The suture interacts with the binding surfaces by means of friction. Friction always acts in the opposite direction of motion. As the suture is drawn to tighten tissue, the frictional interaction opposes this motion. Consequently, more force is needed to achieve the same effect on the tissue. Once the practitioner releases the suture, the motion of the suture changes direction, and so does the frictional forces. Now, the friction forces act to bind the suture to the resilient mechanism by means of the surface or surfaces.

This invention takes advantage of this change in frictional force direction to bind the suture to the resilient means. This is managed by having more than one surface interacting with suture within the receiving receptacle. These surfaces can move relative to one another. The suture, in being tensioned, moves a surface relative to another surface so that less pressure is put on the suture and the suture is free to move. Then, the tension is released from the suture and the suture changes direction, pulling the surfaces in the opposite direction relative to one another. This changes in direction moves the surfaces to put more pressure on the suture, thus binding it in the suture receiving receptacle.

Other embodiments of the invention use mechanical means to draw the surface together, so that sufficient pressure is put on the suture to bind it in the suture receiving receptacle.

The tissue portions comprise biological tissue in the body, including, but not limited to, skin, tendon, bone, ligaments, blood vessels, and organs. The suture may comprise woven, braided, or knitted fibers or metals, or a monofilament, and can be made of any known suture material. The suture may be of any shape, including, but not limited to, round, square, oval, flat (like a strap), or tubular. The shape of the suture for particular embodiments will be discussed more fully hereinbelow.

More particularly, there is provided a surgical tensioning device for dynamically holding two tissue portions in contact with one another. The inventive device comprises a resilient member and a pressure locking mechanism engaging the resilient member. The pressure locking mechanism has a surface for engaging and clamping a length of suture passing therethrough, which is responsive to tension changes applied to the suture to secure the suture in place without a need for knotting the suture. In some embodiments, the resilient member comprises a spring having a base portion and a plurality of extending portions extending from the base portion. An attachment point is disposed on each of the plurality of extending portions. The plurality of extending portions may comprise legs spaced from one another and upstanding from the base portion. The legs each have distal ends, and one of the attachment points is disposed on each of the leg distal ends. The pressure locking mechanism comprises one of the attachment points.

A second one of the attachment points, on a second one of the legs, is adapted to be connected to a first end of a length of suture, and a second end of the length of suture is adapted to be secured within the pressure locking mechanism.

In one particular embodiment, the pressure locking mechanism comprises a tube having an internal cylindrical wall which comprises the aforementioned single surface, with the suture being adapted to pass through a lumen in the tube defined by the internal cylindrical wall. The internal cylindrical wall is adapted to collapse about the suture responsive to tension placed on the suture.

In certain preferred embodiments, the resilient member is fabricated from one of spring tempered stainless steel or titanium, as is the pressure locking mechanism. However, the pressure locking mechanism is fabricated from one of fully annealed spring tempered stainless steel or fully annealed titanium.

In another embodiment of the invention, the pressure locking mechanism comprises a plurality of the aforementioned clamping surfaces. In this embodiment, the pressure locking mechanism comprises a loop having an internal surface defining a channel through which the suture may pass, and an inserting plug which is insertable into the channel. The inserting plug has an external surface, wherein the suture is clamped between the internal surface of the loop and the external surface of the inserting plug. Preferably, one of the internal surface of the loop and the external surface of the inserting plug is textured.

In yet another embodiment of the inventive device, the suture preferably comprises flat or tape suture. The resilient member comprises a spring loop and a plurality of attachment points for securing the suture to the resilient member, and the pressure locking mechanism is disposed at one of the attachment points. The pressure locking mechanism comprises a pin and a pair of flexible arms for supporting the pin, a gap being formed between the pin and a surface of the spring loop for receiving the suture. Wherein when tension in the suture changes, the spring loop moves to clamp the suture between the spring loop surface and the pin.

In another aspect of the invention, there is provided a pressure locking mechanism for securing suture in place at a procedural site. The pressure locking mechanism is adapted for engagement with a resilient member and has a surface for engaging and clamping a length of suture passing therethrough. The surface is responsive to tension changes applied to the suture to secure it in place without a need for knotting the suture. The pressure locking mechanism comprises, in one embodiment, a tube having an internal cylindrical wall which comprises the aforementioned surface, with the suture being adapted to pass through a lumen in the tube defined by the internal cylindrical wall, and the internal cylindrical wall being adapted to collapse about the suture responsive to changes of tension on the suture. In other embodiments, the pressure locking mechanism comprises a plurality of the aforementioned surfaces. In one modified embodiment, the pressure locking mechanism comprises a loop having an internal surface defining a channel through which the suture may pass, and an inserting plug which is insertable into the channel. The inserting plug has an external surface, wherein the suture is clamped between the internal surface of the loop and the external surface of the inserting plug.

In another modified embodiment, flat suture is utilized, and the pressure locking mechanism comprises a pin and a pair of flexible arms for supporting the pin, a gap being formed adjacent to said pin for receiving the suture.

In yet another aspect of the invention, there is disclosed a method for securing together two spaced bodily tissues with a surgical tensioning device comprising a resilient member and a pressure locking device. The method comprises a step of routing one end of a length of suture through both spaced bodily tissues and inserting the suture end into and through the pressure locking device. The suture is then tensioned by pulling on the suture end passing through the pressure locking device. Then the pressure locking device is actuated responsive to changes in tension in the suture by moving at least one surface in the pressure locking device to clamp the suture in position.

The invention, together with additional features and advantages thereof, may best be understood by reference to the following description taken in conjunction with the accompanying illustrative drawings.

DESCRIPTION OF THE PREFERRED EMBODIMENT

Figure 1:
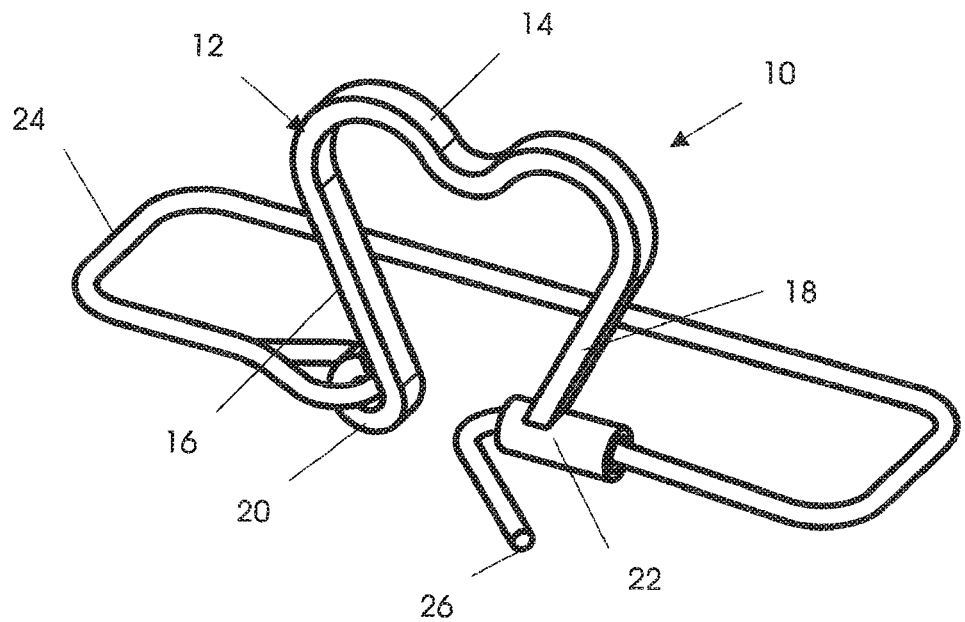
FIG. 1 is an isometric view illustrates one representative embodiment of the device of the present invention.
Figure 2:
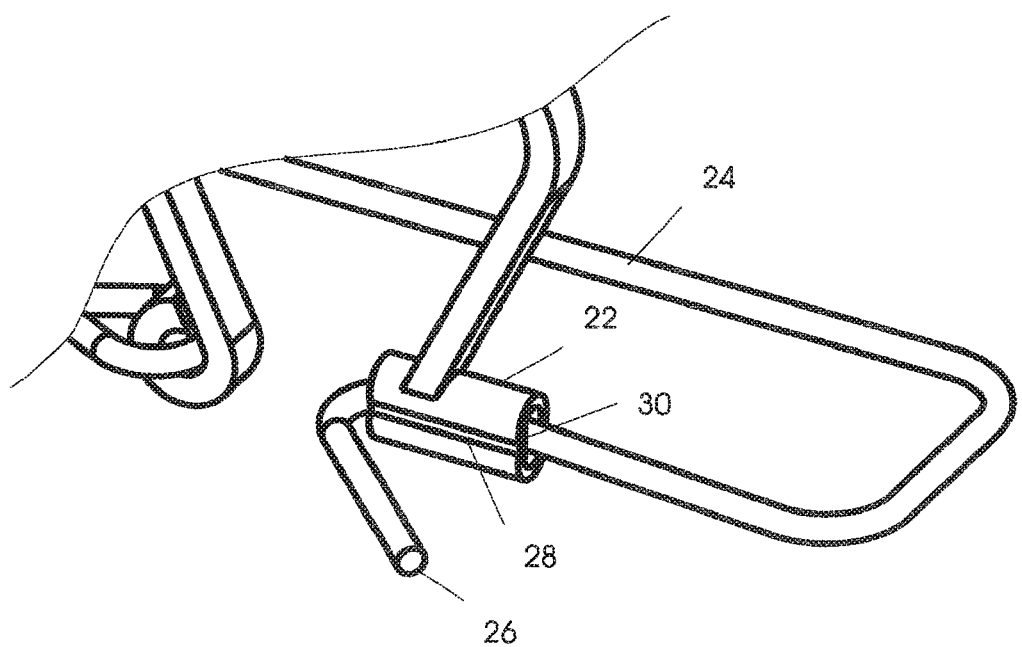
FIG. 2 is an enlarged view of the locking tension device of the embodiment of FIG. 1.

Referring now more particularly to the drawings, there is shown in FIGS. 1-2 one embodiment of a knotless dynamic suturing device 10 which is constructed in accordance with the principles of the present invention. The device 10 is constructed to utilize a single surface to impart a locking pressure on a length of suture, and comprises a resilient member or spring 12, which is generally shaped like the letter "U", with a base portion 14 and upstanding legs 16, 18. Each upstanding leg includes, at its end distal to the base portion 14, respective attachment points 20 and 22. Each attachment point 20, 22 may comprises a loop, hook or pressure locking mechanism as shown.

A length of suture 24 is attached to the attachment point 20 at one end thereof, as shown, to thereby attach the suture 24 to the spring 12. The suture 24 is first woven or stitched into and through tissue with suture end 26 leading the way. A needle may be used to route the suture through tissue. Then, suture 24 is routed into attachment point 22, which comprises a pressure locking mechanism, using the suture end 26. The suture is then brought into tension by pulling on the suture end 26. As the suture 24 is put into tension, two concurrent movements are realized. First, the tissue portions to be approximated are brought to their desired positions, in approximation to one another, and second, the legs 16 and 18 of the device 10 flex apart to store the energy needed in the spring's bridge or base 14, in order to supply continuing tension to the suture, thus keeping the tissue in compression while it heals.

The locking pressure device 22 is fabricated of a tubular material. The pressure is derived by collapsing the tubular walls onto suture 24 by means of an external device. Preferably, this external device comprises a crimping tool, but any suitable tool could be used by the practitioner, at a time during the procedure when the practitioner is ready to lock the suture in place. Collapsing the tubular walls permanently distorts the tube at point 28, such that it permanently locks the suture within a lumen 30 of the tube. Thus, the single surface utilized to pressure lock the suture in place is the internal cylindrical wall of the tube 22. The material utilized to fabricate the legs 16, 18 and the base portion 14 of the spring 12 must be sufficiently resilient to supply the energy storage needed for the inventive device to properly function. The material utilized to fabricate the tube 22 must be sufficiently compliant so as to conform and form around the suture 24. Should both of these materials (for fabricating the spring 12 and tubular pressure locking mechanism 22) be the same, the temper of the material would still be different in order to provide the desired properties. Preferably, the entire device is made of spring tempered stainless steel or titanium, with the locking pressure device 22 being fully annealed to be sufficiently compliant.

Figure 3:
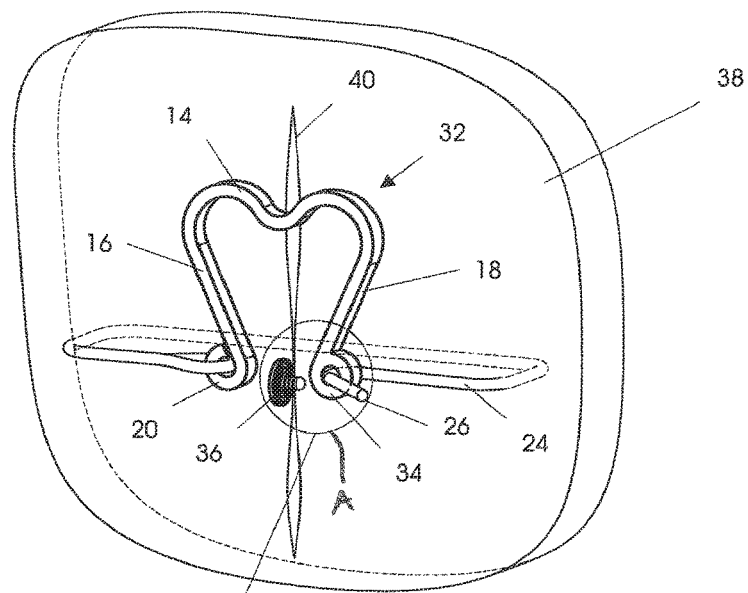
FIG. 3 is a view similar to FIG. 1, illustrating a modified embodiment of the present invention, as used to approximate two tissue portions.

FIGS. 3-6 illustrate a modified embodiment of the present invention, having a pressure locking device which utilizes two surfaces to pressure lock the suture into place. In this embodiment, like elements to those in the FIGS. 1-2 embodiment are designated by like reference numerals. Thus, in FIG. 3, there is shown a device 32 that is designed to utilize two surfaces to generate the locking pressure on the suture 24. The device 32 comprises a pressure locking mechanism 34, comprising a loop, and an inserting plug 36. FIG. 3 shows tissue 38 with a lesion 40 being approximated by the device 32. This application is similar for all three illustrated embodiments, though other applications are appropriate as well. Suture 24 has been routed around tissue 38 and inserted with suture end 26 into the pressure locking mechanism 34. The suture 24 is then brought into tension by pulling on the suture end 26. As tension is brought onto the suture, two concurrent movements are realized. First, the tissue 38 is brought to its desired position, and second, legs 16 and 18 flex apart to store the energy needed in the spring's base or bridge 14 to supply continuing tension to the suture, thus keeping the tissue in compression while it heals. The loop 34 includes a channel defined by an inner-surface 42, through which the suture passes.

Figures 4, 5:
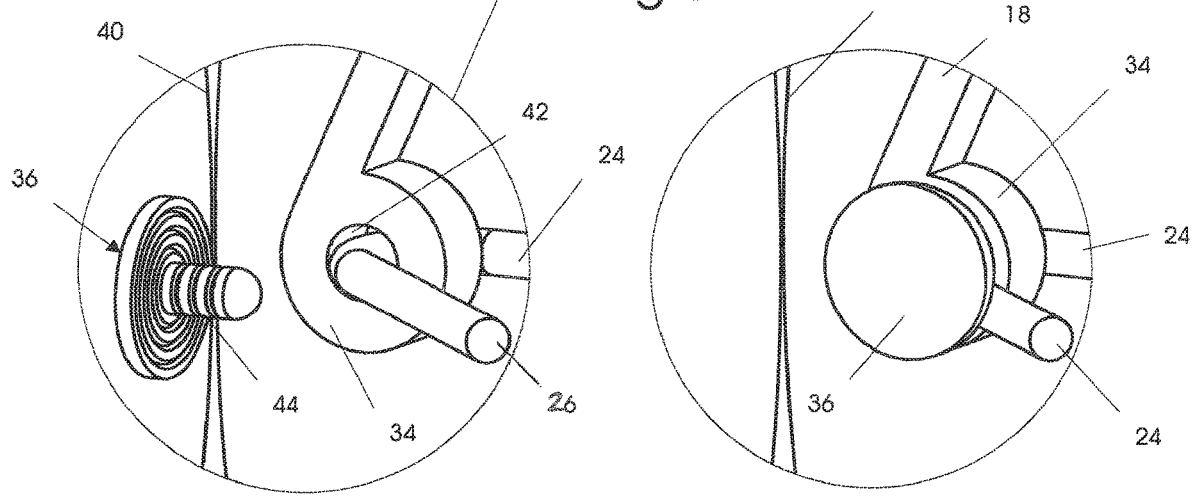
FIG. 4 is a detail view of portion A of FIG. 3.
FIG. 5 is a detail view similar to FIG. 4, illustrating the pressure lock of the embodiment of FIGS. 3-4 in a fully assembled state.
Figure 6:
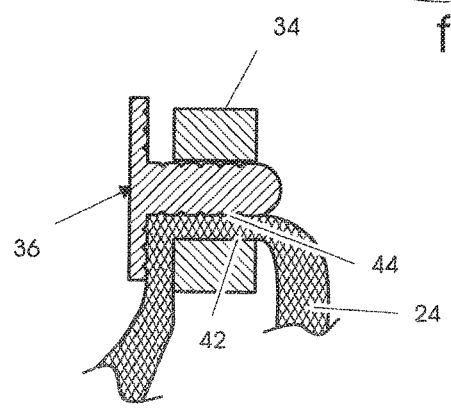
FIG. 6 is a cross-sectional view illustrating the pressure locking function achieved by the embodiment of FIGS. 3-5.

The locking pressure is generated by inserting the plug 36, which comprises an external surface 44, into the interior of the pressure locking mechanism 34, and squeezing the suture 24 between surfaces 42 and 44. FIG. 6 illustrates a cross-section of the suture 24 squeezed in the interface between surfaces 42 and 44. Either of the surfaces 42, 44 may be textured in order to increase the friction on the lock. In this embodiment, as illustrated, surface 44 is textured, so that the plug 36 is pulled in to the interior of the pressure locking mechanism 34 by the tension in the suture 24. FIG. 5 shows the pressure locking mechanism 34 in a fully assembled state.

Figure 7:
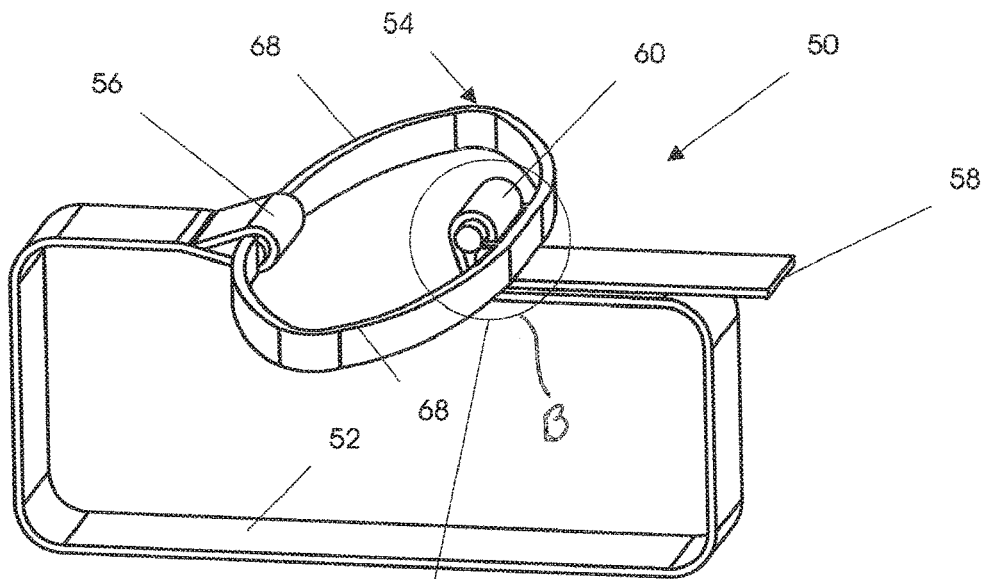
FIG. 7 is an isometric view of another modified embodiment of the invention.
Figure 8:
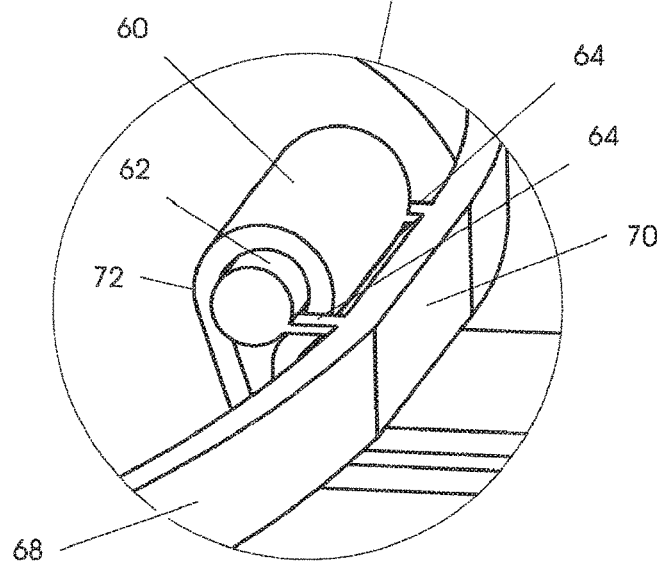
FIG. 8 is a detail view of portion B of FIG. 7.
Figure 9:
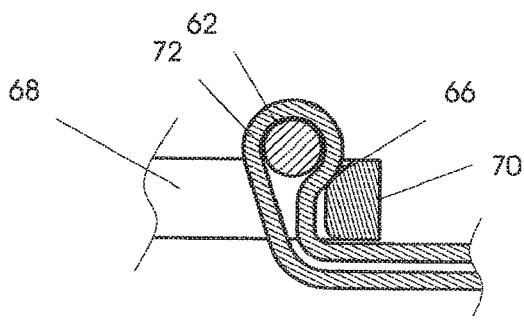
FIG. 9 is a cross-sectional view detailing the pressure locking function achieved by the embodiment of FIGS. 7 and 8.

A third embodiment of the inventive concept is shown in FIGS. 7-9. In this embodiment, pressure is again used to lock the suture, but also, significant frictional resistance is employed while tensioning. This knotless dynamic suturing device 50 is represented in FIG. 7, with FIG. 8 detailing the pressure lock and FIG. 9 showing a cross-section of the detailed interface of FIG. 8. While the invention is not constrained to flat suture, the embodiment 50 makes use of flat or tape suture 52. Flat suture is preferred in situations where the high tensions in the suture require that broad contact is ensured between the suture and the tissue. This broad contact distributes the tension in the suture over a broad area, thus preventing the tension in the suture from damaging tissue. This is an especially important feature when dealing with patients with known poor bone quality, such as diabetic and osteoporotic patients.

As in the above described prior embodiments, the suture 52 is connected to a spring 54 at an attachment point 56. A suture end 58 is routed through the tissue with a needle (not shown), and back to an attachment point 60 where it is routed around a pin 62. Pin 62 is able to float on a pair of flexible arms 64 to permit suture to pass between the pin 62 and a spring surface 66 (FIG. 9). As tension is applied to the suture end 58, and the tissues are brought into compression, spring loops 68 on the spring 54 distend storing energy that will supply substantially constant compression during the tissue healing cycle. Applying tension to the suture end 58 also pushes the pin 62 away from the spring surface 66, thereby decreasing the pressure on the suture in that interface. When tension is released on the suture end 58, the predominate suture tension shifts to the other side of the pin at point 72, thus effectively pushing the pin 62 into the spring surface 66. This action supplies the pressure needed to lock and hold the suture in place.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. A surgical tensioning device for holding two tissue portions in contact with one another, the device comprising:
   a resilient member extending from a first end to a second end;
   a suture attachment member disposed at the first end of the resilient member; and
   a pressure locking mechanism disposed at the second end of the resilient member and including opposing surfaces for engaging and clamping a length of suture to secure the suture in place without a need for knotting the suture, the pressure locking mechanism comprising:

a hook or loop member including a channel sized to allow passage of the length of suture therethrough; and a locking member insertable within the channel.

2. The surgical tensioning device of claim 1, wherein the opposing surfaces of the pressure locking mechanism comprise an internal surface of the hook or loop member that defines the channel and an external surface of the locking member.

3. The surgical tensioning device of claim 2, wherein upon engagement of the locking member with the channel of the hook or loop member, the external surface of the locking member and the internal surface of the hook or loop member generate a locking pressure on the suture.

4. The surgical tensioning device of claim 3, wherein at least one of the external surface and the internal surface is textured to increase friction when the locking member engages the channel of the hook or loop member.

5. The surgical tensioning device of claim 2, wherein the locking member includes a shaft portion configured for insertion within the channel of the hook or loop member.

6. The surgical tensioning device of claim 2, wherein the locking member comprises a plug.

7. The surgical tensioning device of claim 1, wherein the resilient member includes a base portion, a first leg extending from a first end of the base portion, and a second leg extending from a second end of the base portion.

8. The surgical tensioning device of claim 7, wherein the base portion and the first and second legs of the resilient member form a spring element.

9. The surgical tensioning device of claim 7, wherein the resilient member is normally biased such that the first and second legs converge distally towards each other in a first configuration.

10. The surgical tensioning device of claim 9, wherein the suture is configured to be tensioned by pulling on an end of the suture, thereby causing the first and second legs to move from the first configuration to a second configuration in which the first and second legs are flexed apart to store energy in the base portion sufficient to supply continuing tension to the suture.

11. The surgical tensioning device of claim 1, wherein the pressure locking mechanism is operable to squeeze the suture at an interface formed between the opposing surfaces.

12. A surgical tensioning device for holding two tissue portions in contact with one another, the device comprising:
   a resilient member including a base portion, a first leg extending from a first end of the base portion, and a second leg extending from a second end of the base portion;
   a suture attachment member disposed at a first location on the first leg of the resilient member; and
   a pressure locking mechanism disposed at a second location on the second leg of the resilient member; the pressure locking mechanism comprising:
      a hook or loop member including a channel defined by a first surface; and
      a locking member including a second surface;
   wherein the locking member is engageable with the channel of the hook or loop member to clamp a length of suture between the first and second surfaces and to secure the suture in place without a need for knotting the suture.

13. The surgical tensioning device of claim 12, wherein the first surface is an internal surface of the hook or loop member and the second surface is an external surface of the locking member.

14. The surgical tensioning device of claim 13, wherein upon engagement of the locking member with the channel of the hook or loop member, the external surface of the locking member and the internal surface of the hook or loop member generate a locking pressure on the suture.

15. The surgical tensioning device of claim 14, wherein at least one of the external surface and the internal surface is textured to increase friction when the locking member engages the channel of the hook or loop member.

16. The surgical tensioning device of claim 12, wherein the suture is configured to extend from the suture attachment member and through the channel in the hook or loop member.

17. A surgical tensioning device for holding two tissue portions in contact with one another, the device comprising:
   a resilient member extending from a first end to a second end;
   a suture attachment member disposed at the first end of the resilient member;
   a pressure locking mechanism disposed at the second end of the resilient member and comprising:
      a hook or loop member including a channel; and
      a locking member insertable within the channel; and
   a length of suture configured to extend from the suture attachment member and through the channel of the hook or loop member;
   the pressure locking mechanism including at least two surfaces configured to generate a locking pressure on the suture to secure the suture in place without a need for knotting the suture, the at least two surfaces including an internal surface of the hook or loop member that defines the channel and an external surface of the locking member.

* * * * *

UNITED STATES PATENT AND TRADEMARK OFFICE
CERTIFICATE OF CORRECTION

PATENT NO. : 10,765,418 B2
APPLICATION NO. : 15/821486
DATED : September 8, 2020
INVENTOR(S) : Seth A. Foerster It is certified that error appears in the above-identified patent and that said Letters Patent is hereby corrected as shown below:

On the Title Page

In Column 1, under "Related U.S. Application Data", Line 1, delete "(60)" and insert --(63)-- therefor In the Claims In Column 7, Line 4, in Claim 1, delete "insertable:" and insert --insertable-- therefor In Column 8, Line 4, in Claim 12, delete "member;" and insert --member,-- therefor Signed and Sealed this
Eighth Day of December, 2020

Andrei Iancu
*Director of the United States Patent and Trademark Office*